United States Patent [19]

Diana et al.

[11] Patent Number: 5,633,388
[45] Date of Patent: May 27, 1997

[54] COMPOUNDS, COMPOSITIONS AND METHODS FOR TREATMENT OF HEPATITIS C

[75] Inventors: Guy D. Diana, Pottstown; Thomas R. Bailey, Phoenixville, both of Pa.

[73] Assignee: Viropharma Incorporated, Malvern, Pa.

[21] Appl. No.: 625,717

[22] Filed: Mar. 29, 1996

[51] Int. Cl.$^6$ .................. C07D 403/12; A61K 31/415
[52] U.S. Cl. ......................................................... 548/305.7
[58] Field of Search .............................. 514/393, 394, 514/415; 548/302.7, 305.4, 305.7, 455, 309.7

[56] References Cited

U.S. PATENT DOCUMENTS

| | | | |
|---|---|---|---|
| 5,414,010 | 5/1995 | Downing et al. | 514/316 |
| 5,459,144 | 10/1995 | Girijavallabhan et al. | 514/269 |
| 5,486,525 | 1/1996 | Summers, Jr. et al. | 514/303 |
| 5,493,011 | 2/1996 | Jung et al. | 534/751 |
| 5,496,826 | 3/1996 | Watson et al. | 514/303 |
| 5,552,426 | 9/1996 | Lunn et al. | 514/394 |

OTHER PUBLICATIONS

Singh et al., "Synthesis of newer N–Mannich bases of benzazoles incorporating 2–(4–aminophenyl) 5 or (6) substituted benzimidazoles as potential antiviral agents", Indian Drugs, 23(10), pp. 542–544, (1986).
Alcade et al., J. Org. Chem., 52: 5009–5015 (1987).
Amiel, Recent Results in Cancer Research, 21: 41–53 (1969).
Choo et al., Science, 244: 359–362 (1989).
De Clercq et al., J. Med. Chem., 23(7):787–795 (1980).
Kim et al., Biochem. Biophys. Res. Comm., 214: 60–68 (1995).
Lain et al., Nucleic Acid Res., 18(23): 7003–7006 (1991).
Marcus et al., Cancer Research, 45(1): 112–115 (1985).
Amiel et al., Eur. J. Cancer, 3(1): 47–65 (1967) [with English Abstract].
Warrener et al., J. Viro., 69: 1720–1726 (1995).

Primary Examiner—Mukund J. Shah
Assistant Examiner—Deepak R. Rao
Attorney, Agent, or Firm—Dann, Dorfman, Herrell and Skillman

[57] ABSTRACT

Heterocyclic substituted carboxamides are useful in prophylaxis and treatment of hepatitis C virus infections.

23 Claims, No Drawings

COMPOUNDS, COMPOSITIONS AND METHODS FOR TREATMENT OF HEPATITIS C

FIELD OF THE INVENTION

The present invention relates to compounds, compositions and methods for the treatment of hepatitis C virus (HCV) infection. In particular, the present invention provides novel heterocyclic-substituted carboxamides and analogues thereof, pharmaceutical compositions containing such compounds and methods for using the compounds in treating HCV and other viral diseases.

BACKGROUND OF THE INVENTION

HCV, which is found in all parts of the world, has been characterized as single-stranded RNA virus of about 9.5 kilobases in length. Choo et al., *Science*, 244: 395–62 (1989).

Surgery patients and others requiring blood transfusions, and especially those having suppressed immune systems, resulting, for example, from drugs administered in connection with organ transplantation, are at risk of developing HCV infection, which is the primary cause of transfusion-associated hepatitis in the world today. It has been estimated that posttransfusion hepatitis C may be responsible for up to 3,000 annual cases of chronic active hepatitis or cirrhosis of the liver in the U.S. alone. Hemodialysis patients, as well as intravenous drug abusers are other groups which are at risk for acquiring HCV infection.

The mechanism by which HCV replicates has not been thoroughly elucidated, thus hindering research aimed at developing an effective vaccine. Immune globulin has been reported for prophylaxis of transfusion-associated viral hepatitis. However, the Centers for Disease Control do not presently recommend immune globulin for this purpose.

Various clinical studies have been conducted with the goal of identifying pharmaceutical agents capable of effectively treating HCV infection in patients afflicted with chronic hepatitis C. These studies have involved the use of dideoxy-nucleoside analogues and interferon-alpha, alone and in combination therapy with other anti-viral substances. Such studies have shown, however, that substantial numbers of the participants do not respond to this therapy, and of those that do respond favorably, a large proportion were found to relapse after termination of treatment.

Thus, a need exists for new anti-viral agents and treatments for HCV infection that overcome the limitations of existing pharmaceutical therapies. Insofar as is known, heterocyclic-substituted carboxamides and analogues thereof have not been previously reported as being useful for the treatment of HCV.

SUMMARY OF THE INVENTION

In accordance with one aspect, the present invention provides compounds, including isomers, having the following structure:

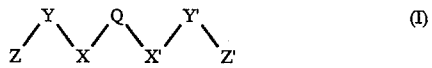

(I)

in which Q is a divalent moiety selected from the group consisting of straight or branched, unsubstituted or substituted $C_1$–$C_{12}$ alkylene, straight or branched, unsubstituted or substituted $C_2$–$C_{12}$ alkenylene, straight or branched, unsubstituted or substituted $C_1$–$C_{12}$ alkylene interrupted with oxygen, nitrogen or sulfur, straight or branched, unsubstituted or substituted $C_2$–$C_{12}$ alkenylene interrupted with oxygen, nitrogen or sulfur, with the alkylene and alkenylene moiety substituents being selected from at least one of the group consisting of alkyl ($C_1$–$C_6$), amino, alkylamino, dialkylamino or acetamido, or an arylene moiety of the formula:

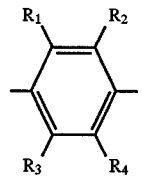

in which $R_1$, $R_2$, $R_3$ and $R_4$ are the same or different and represent substituents selected from the group consisting of hydrogen, alkyl ($C_1$–$C_6$), halogen, hydroxy, alkoxy, carboxy, carbalkoxy, alkylthio, alkylsulfinyl, alkylsulfonyl, amino, acetamido, sulfonamido, alkylamino, dialkylamino and $NO_2$; X and X' may be the same or different and represent divalent linkages selected from the group consisting of: —NR—(C=O)—, —(C=O)—NR'—, —NR"—$CH_2$—, or —$CH_2$—NR'"—, in which R, R', R" and R'" represent hydrogen or an alkyl group ($C_1$–$C_6$); Y and Y' represent the same or different divalent moieties selected from the group consisting of unsubstituted or substituted alkylene ($C_3$–$C_5$), with the alkylene substituents being selected from the group consisting of alkyl ($C_1$–$C_6$), amino, alkylamino, dialkylamino or acetamido, and unsubstituted or substituted phenylene, with the phenylene substituents being selected from the group consisting of hydrogen, alkyl ($C_1$–$C_6$), halogen, hydroxy, alkoxy, carboxy, carbalkoxy, alkylthio, alkylsulfinyl, alkylsulfonyl, amino, acetamido, sulfonamido, alkylamino, dialkylamino and $NO_2$; Z and Z' represent the same or different substituent selected from the group consisting of those substituents having the formula:

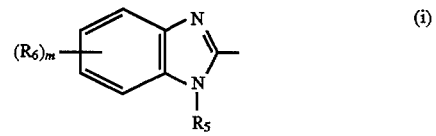

(i)

in which $R_5$ represents a substituent selected from the group consisting of hydrogen, alkyl ($C_1$–$C_6$) and acyl, and each $R_6$ is the same or different and represents a substituent selected from the group consisting of hydrogen, alkyl ($C_1$–$C_6$), halogen, hydroxy, alkoxy, carboxy, carbalkoxy, alkylthio, alkylsulfinyl, alkylsulfonyl, amino, acetamido, sulfonamido, alkylamino, dialkylamino and $NO_2$, and m is 1–4,

(ii)

in which $R_a$ represents a substituent selected from the group consisting of hydrogen, alkyl ($C_1$–$C_6$) and acyl,

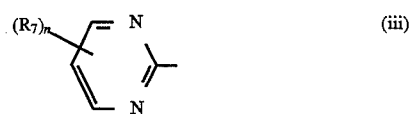

(iii)

in which each $R_7$ is the same or different and represents a substituent selected from the group consisting of hydrogen, alkyl ($C_1$–$C_6$), halogen, hydroxy, alkoxy, carboxy, carbalkoxy, alkylthio, alkylsulfinyl, alkylsulfonyl, amino, acetamido, sulfonamido, alkylamino, dialkylamino and $NO_2$, and n is 1–3,

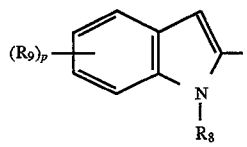

in which $R_8$ represents a substituent selected from the group consisting of hydrogen, alkyl ($C_1$–$C_6$) and acyl and each $R_9$ is the same or different and represents a substituent selected from the group consisting of hydrogen, alkyl ($C_1$–$C_6$), halogen, hydroxy, alkoxy, carboxy, carbalkoxy, alkylthio, alkylsulfinyl, alkylsulfonyl, amino, acetamido, sulfonamido, alkylamino, dialkylamino and $NO_2$, and p is 1–4, or

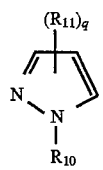

in which $R_{10}$ represents a substituent selected from the group consisting of hydrogen, alkyl ($C_1$–$C_6$) and acyl, and each $R_{11}$ is the same or different and represents a substituent selected from the group consisting of alkyl ($C_1$–$C_6$), alkoxy, carboxy, carbalkoxy, carboxamide, halogen, and q is 1 or 2; and the isomers and pharmaceutically acceptable salts of said compound.

In accordance with another aspect, the present invention provides a class of intermediates which are useful in preparing compounds of formula I, above. The intermediates of alkyl ($C_1$–$C_6$), halogen, hydroxy, alkoxy, carboxy, carbalkoxy, alkylthio, alkylsulfinyl, alkylsulfonyl, amino, acetamido, sulfonamido, alkylamino, dialkylamino and $NO_2$, with s being 1–4.

According to still another aspect, the present invention provides pharmaceutical compositions comprising one or more of the above-described carboxamide derivatives in combination with a pharmaceutically acceptable carrier medium.

In accordance with yet another aspect, the present invention provides a method for treating viral hepatitis C infections in mammalian hosts by administering an effective amount of the compounds of the invention to a patient susceptible to hepatitis C infection or suffering from such an infection.

DETAILED DESCRIPTION OF THE INVENTION

The compounds of the invention can be conveniently prepared from known starting materials according to the general reaction scheme A illustrated below. Intermediate $I_A$ was prepared according to the procedure given in E. Acalade et al., *J. Org. Chem.* 52:5009–15 (1987). Specific embodiments of anti-hepatitis C compounds within the scope of the invention are exemplified below.

REACTION SCHEME A

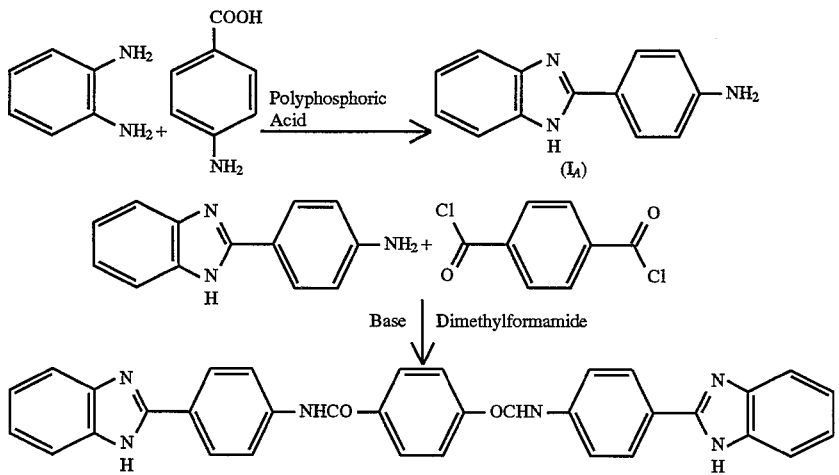

the invention have the structure:

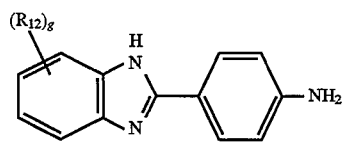

in which each $R_{12}$ is the same or different and represents a substituent selected from the group consisting of hydrogen, The reverse amide compounds of the invention can be conveniently prepared from known starting materials according to the general reaction scheme B illustrated below.

REACTION SCHEME B

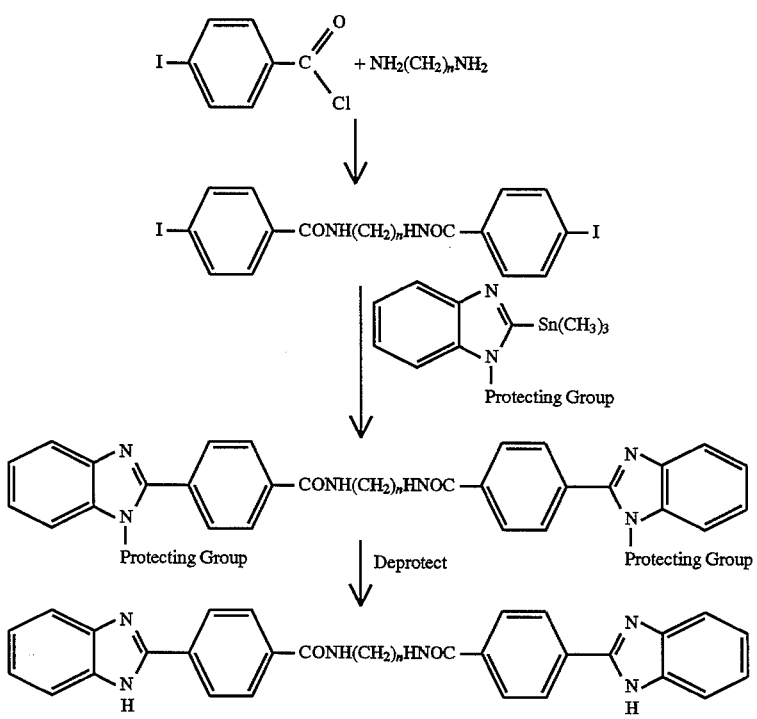

Suitable protecting groups for use in carrying out reaction scheme B include, for example, dialkylaminomethyl or pyrrolidinomethyl groups.

Preparation of compounds of the invention containing different Q moieties can be achieved by substitution of the appropriate acid chloride and amines in the above reaction schemes.

In vitro studies demonstrating the usefulness of the compounds of the invention as antiviral agents have been performed. Anti-viral activity was measured on the basis of inhibition of helicase activity. The biological studies of the anti-viral activity of the compounds of the invention are described below.

In the compounds represented by formula I, above, Q preferably represents a divalent moiety having 12 or less carbon atoms, which is selected from the group of alkylene moieties, (e.g., methylene, ethylene, propylene, butylene, pentylene or the like), alkenylene moieties (e.g., ethenylene, propenylene or the like) or an unsubstituted or substituted phenylene moiety; X and X' are preferably amide linkages; Y and Y' are preferably divalent unsubstituted or substituted phenylene moieties and Z and Z' are preferably unsubstituted and substituted benzimidazole substituents. When Q is a divalent alkylene or alkenylene moiety, it may be interrupted by oxygen, sulfur or nitrogen. Representative examples of such moieties include —$CH_2$—$CH_2$—O—$CH_2$—$CH_2$—, —$CH_2$—$CH_2$—S—$CH_2$—$CH_2$—, —$CH_2$-CH2—NH—$CH_2$—$CH_2$—, —$(CH_2)_2$—O—$(CH_2)_2$—O—$(CH_2)_2$—O—$(CH_2)_2$—, —CH=CH—$CH_2$—O—$CH_2$—CH=CH—and —CH=CH—$CH_2$—S—$CH_2$—CH=CH—.

The term "alkyl" as used herein refers to aliphatic hydrocarbon radicals of one to six carbon atoms in length. Similarly, the term "alkyl", or any variation thereof, used in combination form to name substituents such as carbalkoxy, alkoxy, alkylthio, alkylamino, alkylsulfinyl or alkylsulfonyl also refers to aliphatic hydrocarbon radicals of one to six carbon atoms in length, and preferably of one to four carbon atoms in length.

Among the particularly preferred embodiments of the invention are compounds, including isomeric forms, having the formula:

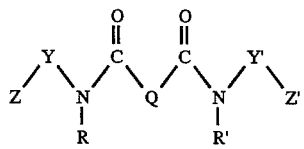

in which Q is an arylene moiety of the formula:

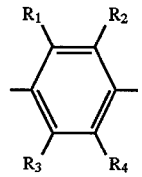

in which $R_1$, $R_2$, $R_3$ and $R_4$ are the same or different and represent substituents selected from the group consisting of hydrogen, alkyl ($C_1$-$C_6$), halogen, hydroxy, alkoxy, carboxy, carbalkoxy, alkylthio, alkylsulfinyl, alkylsulfonyl, amino, acetamido, sulfonamido, alkylamino, dialkylamino and $NO_2$; R and R' are the same or different and represent hydrogen or an alkyl ($C_1$-$C_6$) group; Y and Y' represent the same or different divalent moieties selected from the group consisting of alkylene ($C_3$-$C_5$) and phenylene, with Y and Y' moieties being unsubstituted or substituted with at least one alkyl group ($C_1$-$C_6$); Z and Z' represent the same or different substituent having the formula:

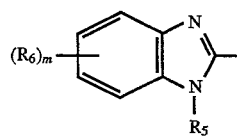

in which R₅ represents a substituent selected from the group consisting of hydrogen, alkyl ($C_1$–$C_6$) and acyl, and each R₆ is the same or different and represents a substituent selected from the group consisting of hydrogen, alkyl ($C_1$–$C_6$), halogen, hydroxy, alkoxy, carboxy, carbalkoxy, alkylthio, alkylsulfinyl, alkylsulfonyl, amino, acetamido, sulfonamido, alkylamino, dialkylamino and $NO_2$, with m being 1–4, and the isomers and pharmaceutically acceptable salts of this compound.

Also preferred are compounds, including isomeric forms, having the formula:

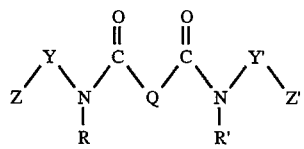

in which Q is a divalent moiety selected from the group consisting of straight or branched, unsubstituted or substituted $C_1$–$C_{12}$ alkylene, straight or branched, unsubstituted or substituted $C_2$–$C_{12}$ alkenylene, straight or branched, unsubstituted or substituted $C_1$–$C_{12}$ alkylene interrupted with oxygen, nitrogen or sulfur, straight or branched, unsubstituted or substituted $C_2$–$C_{12}$ alkenylene interrupted with oxygen, nitrogen or sulfur, with the alkylene and alkenylene moiety substituents being selected from at least one of the group consisting of alkyl ($C_1$–$C_6$), amino, alkylamino, dialkylamino or acetamido; R and R' are the same or different and represent hydrogen or an alkyl ($C_1$–$C_6$) group; Y and Y' represent the same or different divalent moieties selected from the group consisting of alkylene ($C_3$–$C_5$) and phenylene, with the Y and Y' moieties being unsubstituted or substituted with at least one alkyl group ($C_1$–$C_6$); Z and Z' represent the same or different substituent having the formula:

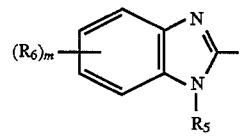

in which R₅ represents a substituent selected from the group consisting of hydrogen, alkyl ($C_1$–$C_6$) and acyl, and each R₆ is the same or different and represents a substituent selected from the group consisting of hydrogen, alkyl ($C_1$–$C_6$), halogen, hydroxy, alkoxy, carboxy, carbalkoxy, alkylthio, alkylsulfinyl, alkylsulfonyl, amino, acetamido, sulfonamido, alkylamino, dialkylamino and NOR, with m being 1–4, and the isomers and pharmaceutically acceptable salts of this compound.

Isomers of the arylene Q moiety such as the phthalic acid chloride or the isophthalic acid chloride can be used in preparing compounds of the invention. Isomers of the alkenylene Q moiety such as the cis or trans isomers can also be used.

As previously noted, the compounds of formula I, above, including their pharmaceutically acceptable salts, exhibit antiviral activity against hepatitis C virus.

The compounds of the invention can form salts with inorganic and organic acids, including, for example, acids such as hydrochloric acid, hydrobromic acid and methanesulfonic acid.

The pharmaceutically acceptable salts of the compounds of formulas I and II are prepared following procedures which are familiar to those skilled in the art.

The antiviral pharmaceutical compositions of the present invention comprise one or more of the compounds of formula I, above, as the active ingredient in combination with a pharmaceutically acceptable carrier medium or auxiliary agent.

The composition may be prepared in various forms for administration, including tablets, caplets, pills or dragees, or can be filled in suitable containers, such as capsules, or, in the case of suspensions, filled into bottles. As used herein, "pharmaceutically acceptable carrier medium" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences*, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the anti-viral compounds of the invention, such as by producing any undesirable biological effect or otherwise interacting in a deleterious manner with any other component(s) of the pharmaceutical composition, its use is contemplated to be within the scope of this invention. In the pharmaceutical compositions of the invention, the active agent may be present in an amount of at least 0.5% and not more than 90% by weight based on the total weight of the composition, including carrier medium and/or auxiliary agent(s). Preferably, the proportion of active agent varies between 5%–50% by weight of the composition. Pharmaceutical organic or inorganic solid or liquid carrier media suitable for enteral or parenteral administration can be used to make up the composition. Gelatine, lactose, starch, magnesium, stearate, talc, vegetable and animal fats and oils, gum, polyalkylene glycol, or other known excipients or diluents for medicaments may all be suitable as carrier media.

The compounds of the invention may be administered using any amount and any route of administration effective for attenuating infectivity of the hepatitis C virus. Thus, the expression "therapeutically effective amount", as used herein, refers to a nontoxic but sufficient amount of the antiviral agent to provide the desired treatment of viral infection. The exact amount required will vary from subject to subject, depending on the species, age, and general condition of the subject, the severity of the infection, the particular antiviral agent, its mode of administration, and the like. The anti-hepatitis C compounds are preferably formulated in dosage unit form for ease of administration and uniformity of dosage. Dosage unit form as used herein refers to a physically discrete unit of anti-viral agent appropriate for the patient to be treated. Each dosage should contain the quantity of active material calculated to produce the desired therapeutic effect either as such, or in association with the selected pharmaceutical carrier medium. Typically, the antiviral compounds of the invention will be administered in dosage units containing from about 1 mg to about 500 mg of the anti-viral agent by weight of the composition with a range of about 1 mg to about 50 mg being preferred.

The compounds of the invention may be administered orally, parenterally, such as by intramuscular injection, intraperitoneal injection, intravenous infusion or the like, depending on the severity of the infection being treated. The compounds of the invention may be administered orally or parenterally at dosage levels of about 0.1 to 50 and preferably from about 1 to about 10 mg/kg, of patient body weight per day, one or more times a day, to obtain the desired therapeutic effect.

Although the carboxamide derivatives described herein can be administered to any patient which is susceptible to hepatitis C infection, the compounds are intended for the treatment of mammalian hosts, and especially humans.

The compounds of the invention will typically be administered from one to four times a day so as to deliver the above-mentioned daily dosage. However, the exact regimen for administration of the compounds and compositions described herein will necessarily be dependent on the needs of the individual patient being treated, the type of treatment administered and the judgment of the attending physician.

In view of the inhibitory effect on helicase enzyme activity produced by the compounds of the invention, it is anticipated that these compounds will be useful not only for therapeutic treatment of infection, but for hepatitis C viral prophylaxis, as well. The above-noted dosages will be essentially the same whether for treatment or prophylaxis of hepatitis C infection.

The following examples are provided to describe the invention in further detail. These examples, which set forth the best mode presently contemplated for carrying out the invention, are intended to illustrate and not to limit the invention.

Examples 1 to 8 illustrate the chemical synthesis of the compounds of the invention.

EXAMPLE 1

Preparation of 2-(4-aminophenyl)-benzimidazole

This intermediate was prepared according to the procedure given in E. Acalade et al., *J. Org. Chem.* 52:5009–15 (1987). A mixture of 3.21 g (0.0247 moles) of O-phenylenediamine, 3.93 g (0.0287 moles) of 4-aminobenzoic acid and 42 g of polyphosphoric acid was heated to 195° C. for 5 hours. After cooling to room temperature, the reaction mixture was diluted with 180 mL of water and basified to pH 8 with solid potassium carbonate. The resulting precipitate was collected, washed with water and dried to give 4.56 g of product.

EXAMPLE 2

Preparation of N,N'-bis[4-(2-benzimidazolyl) phenyl]-1,4-benzenedicarboxamide

A mixture of 0.88 g (4.35 mmoles) of terephthaloyl chloride, 2.0 g (9.57 mmoles) of 2-(4-aminophenyl) benzimidazole and 3.4 mL of N,N-diisopropylethylamine in 27 mL of dimethylformamide was stirred for 4 hours at room temperature. After the addition of 30 mL of water, a solid separated which was washed with water and dried to give 380 mg of product.

EXAMPLE 3

Preparation of N,N'-bis[4-(2-benzimidazolyl) phenyl]-1,6-hexanedicarboxamide

To a solution of 1.71 g (8.2 mmole) of 2-(4-aminophenyl) benzimidazole and 0.75 g (4.1 mmole) of adipoyl chloride in 23 mL of dry dimethylformamide was added at 0° C. 2.12 mL of N,N-diisopropylethylamine. The temperature was allowed to rise to ambient temperature and left for 12 hours. The addition of 100 mL of water resulted in the precipitation of a solid which was collected, washed with water and dried to give 619 mg of product.

EXAMPLE 4

Preparation of N,N'-bis[4-(2-benzimidazolyl) phenyl]-1,4-butanedicarboxamide

This compound is synthesized and purified according to the general method given in Example 3; however, succinyl chloride is used in the synthesis instead of adipoyl chloride.

EXAMPLE 5

Preparation of N,N'-bis[4-(2-benzimidazolyl) phenyl]-1,8-octanedicarboxamide

This compound is synthesized and purified according to the general method given in Example 3; however, the diacid chloride of octanedioic acid is used in the synthesis instead of adipoyl chloride.

EXAMPLE 6

Preparation of N,N'-bis[4-(2-benzimidazolyl) phenyl]-1,9-nonanedicarboxamide

This compound is synthesized and purified according to the general method given in Example 3; however, azelaoyl chloride is used in the synthesis instead of adipoyl chloride.

EXAMPLE 7

Preparation of N,N'-bis[4-(2-benzimidazolyl) phenyl]-1,10-decanedicarboxamide

This compound is synthesized and purified according to the general method given in Example 3; however, the diacid chloride of sebacic acid is used in the synthesis instead of adipoyl chloride.

EXAMPLE 8

Preparation of N,N'-bis[4-(2-benzimidazolyl) phenyl]-1,4-butenedicarboxamide

This compound is synthesized and purified according to the general method given in Example 3; however, fumaroyl chloride is used in the synthesis instead of adipoyl chloride.

Example 9 illustrates the efficacy of compounds of the invention in inhibiting the viral helicase activity.

EXAMPLE 9

Assay for Helicase Inhibition

The helicase inhibition assay was performed according to methodology of the type described, for example, in: Lain et al., *Nucleic Acids Res.* 18:7003–7006 (1991); Warrener et al., *J. Virol.* 69:1720–1726 (1995); Kim et al., *Biochem. Biophys. Res. Comm.* 160–166 (1995). The values given in Table 1 represent the average of three test results in which the concentrations of anti-viral compound required to achieve a 50% inhibition of helicase activity ($IC_{50}$) were measured.

TABLE 1

| Example Number | $IC_{50}$ (µM) |
| --- | --- |
| 2 | 10 |
| 3 | 0.7 |
| 4 | 0.7 |

TABLE 1-continued

| Example Number | IC$_{50}$ (μM) |
| --- | --- |
| 5 | 0.7 |
| 6 | 0.7 |
| 7 | 0.7 |
| 8 | 0.7 |

The relatively low concentrations of anti-viral compounds required to achieve 50% inhibition of the viral helicase activity tend to show that the compounds of the invention are effective at interfering with propagation of HCV.

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:

1. A compound having the formula:

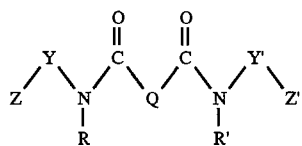

wherein Q is an arylene moiety of the formula:

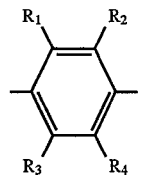

wherein $R_1$, $R_2$, $R_3$ and $R_4$ are the same or different and represent substituents selected from the group consisting of hydrogen, alkyl ($C_1$–$C_6$), halogen, hydroxy, alkoxy, carboxy, carbalkoxy, alkylthio, alkylsulfinyl, alkylsulfonyl, amino, acetamido, sulfonamido, alkylamino, dialkylamino and $NO_2$; R and R' are the same or different and represent hydrogen or an alkyl ($C_1$–$C_6$) group; Y and Y' represent the same or different divalent moieties selected from the group consisting of alkylene ($C_3$–$C_5$) and phenylene, said Y and Y' moieties being unsubstituted or substituted with at least one alkyl group ($C_1$–$C_6$); Z and Z' represent the same or different substituent having the formula:

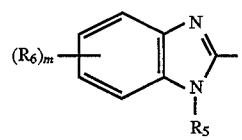 (i)

wherein $R_5$ represents a substituent selected from the group consisting of hydrogen, alkyl ($C_1$–$C_6$) and acyl, and each $R_6$ is the same or different and represents a substituent selected from the group consisting of hydrogen, alkyl ($C_1$–$C_6$), halogen, hydroxy, alkoxy, carboxy, carbalkoxy, alkylthio, alkylsulfinyl, alkylsulfonyl, amino, acetamido, sulfonamido, alkylamino, dialkylamino and $NO_2$, with m being 1–4, and the isomers and pharmaceutically acceptable salts of said compound.

2. The compound N,N'-4-[(2-benzimidazole)phenyl]-1,4-benzenedicarboxamide and the pharmaceutically acceptable salts of said compound, as claimed in claim 1.

3. A compound having the formula:

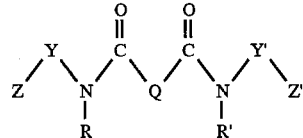

wherein Q is a divalent moiety selected from the group consisting of straight or branched, unsubstituted or substituted $C_1$–$C_{12}$ alkylene, straight or branched, unsubstituted or substituted $C_2$–$C_{12}$ alkenylene, straight or branched, unsubstituted or substituted $C_1$–$C_{12}$ alkylene interrupted with oxygen, nitrogen or sulfur, straight or branched, unsubstituted or substituted $C_2$–$C_{12}$ alkenylene interrupted with oxygen, nitrogen or sulfur, said alkylene and alkenylene moiety substituents being selected from at least one of the group consisting of alkyl ($C_1$–$C_6$), amino, alkylamino, dialkylamino or acetamido; R and R' are the same or different and represent hydrogen or an alkyl ($C_1$–$C_6$) group; Y and Y' represent the same or different divalent moieties selected from the group consisting of alkylene ($C_3$–$C_5$) and phenylene, said Y and Y' moieties being unsubstituted or substituted with at least one alkyl group ($C_1$–$C_6$); Z and Z' represent the same or different substituent having the formula:

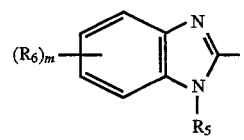 (i)

wherein $R_5$ represents a substituent selected from the group consisting of hydrogen, alkyl ($C_1$–$C_6$) and acyl, and each $R_6$ is the same or different and represents a substituent selected from the group consisting of hydrogen, alkyl ($C_1$–$C_6$), halogen, hydroxy, alkoxy, carboxy, carbalkoxy, alkylthio, alkylsulfinyl, alkylsulfonyl, amino, acetamido, sulfonamido, alkylamino, dialkylamino and $NO_2$, with m being 1–4, and the isomers and pharmaceutically acceptable salts of said compound.

4. The compound N,N'-4-[(2-benzimidazole)phenyl]-1,4-butanedicarboxamide and the pharmaceutically acceptable salts of said compound, as claimed in claim 3.

5. The compound N,N'-4-[(2-benzimidazole)phenyl]-1,6-hexanedicarboxamide and the pharmaceutically acceptable salts of said compound, as claimed in claim 3.

6. The compound N,N'-4-[(2-benzimidazole)phenyl]-1,8-octanedicarboxamide and the pharmaceutically acceptable salts of said compound, as claimed in claim 3.

7. The compound N,N'-4-[(2-benzimidazole)phenyl]-1,9-nonanedicarboxamide and the pharmaceutically acceptable salts of said compound, as claimed in claim 3.

8. The compound N,N'-4-[(2-benzimidazole)phenyl]-1,10-decanedicarboxamide and the pharmaceutically acceptable salts of said compound, as claimed in claim 3.

9. The compound N,N'-4-[(2-benzimidazole)phenyl]-1,4-butenedicarboxamide and the pharmaceutically acceptable salts of said compound, as claimed in claim 3.

10. A pharmaceutical composition for treating hepatitis C virus infection, said composition comprising a compound as claimed in claims 1 and 3 in an amount effective to attenuate infectivity of said virus, and a pharmaceutically acceptable carrier medium.

11. A composition as claimed in claim 10 in the form of a solid with a pharmaceutically acceptable excipient.

12. A composition as claimed in claim 10 in the form of a liquid with a pharmaceutically acceptable diluent.

13. A composition as claimed in claim 10 comprising from about 1 to about 50 mg of said compound by weight of said composition.

14. A method of treatment of hepatitis C virus infection in a patient in need of said treatment, said method comprising administering to said patient a therapeutically effective amount of a compound as claimed in claims 1 or 3.

15. A method as claimed in claim 14, wherein said compound is administered in unit dosage form containing about 1 to about 10 mg of said compound per kilogram of patient body weight per day.

16. A method as claimed in claim 15, wherein said unit dosage includes a pharmaceutically acceptable carrier medium.

17. A method as claimed in claim 14, wherein said compound is administered parenterally.

18. A method as claimed in claim 14, wherein said compound is administered orally.

19. A method of preventing hepatitis C virus infection in a host susceptible to said infection, said method comprising administering to said host a prophylactically effective amount of a compound as claimed in claims 1 or 3.

20. A method as claimed in claim 19, wherein said compound is administered in unit dosage form containing about 1 to about 10 mg of said compound per kilogram of patient body weight per day.

21. A method as claimed in claim 20, wherein said unit dosage includes a pharmaceutically acceptable carrier medium.

22. A method as claimed in claim 19, wherein said composition is administered parenterally.

23. A method as claimed in claim 19, wherein said composition is administered orally.

* * * * *